US011208373B2

(12) United States Patent
Heidemann et al.

(10) Patent No.: US 11,208,373 B2
(45) Date of Patent: *Dec. 28, 2021

(54) METHOD FOR THE PRODUCTION OF ETHYLENEAMINES

(71) Applicant: BASF SE, Ludwigshafen am Rhein (DE)

(72) Inventors: Thomas Heidemann, Ludwigshafen am Rhein (DE); Barbara Becker, Ludwigshafen am Rhein (DE); Eva Koch, Ludwigshafen am Rhein (DE); Johann-Peter Melder, Ludwigshafen am Rhein (DE); Hermann Luyken, Ludwigshafen am Rhein (DE)

(73) Assignee: BASF SE, Ludwigshafen am Rhein (DE)

( * ) Notice: Subject to any disclaimer, the term of this patent is extended or adjusted under 35 U.S.C. 154(b) by 0 days.

This patent is subject to a terminal disclaimer.

(21) Appl. No.: 16/619,976

(22) PCT Filed: May 24, 2018

(86) PCT No.: PCT/EP2018/063591
§ 371 (c)(1),
(2) Date: Dec. 6, 2019

(87) PCT Pub. No.: WO2018/224316
PCT Pub. Date: Dec. 13, 2018

(65) Prior Publication Data
US 2020/0131111 A1 Apr. 30, 2020

(30) Foreign Application Priority Data
Jun. 9, 2017 (EP) .................................. 17175136.5

(51) Int. Cl.
| | | |
|---|---|---|
| *C07C 209/16* | (2006.01) | |
| *B01J 23/89* | (2006.01) | |
| *B01J 21/04* | (2006.01) | |
| *B01J 21/06* | (2006.01) | |
| *B01J 35/02* | (2006.01) | |
| *B01J 37/02* | (2006.01) | |
| *B01J 37/08* | (2006.01) | |

(52) U.S. Cl.
CPC ............. *C07C 209/16* (2013.01); *B01J 21/04* (2013.01); *B01J 21/066* (2013.01); *B01J 23/8913* (2013.01); *B01J 35/026* (2013.01); *B01J 37/0203* (2013.01); *B01J 37/0213* (2013.01); *B01J 37/0236* (2013.01); *B01J 37/086* (2013.01); *B01J 37/088* (2013.01)

(58) Field of Classification Search
CPC .... C07C 209/16; B01J 23/8913; B01J 35/026
See application file for complete search history.

(56) References Cited

U.S. PATENT DOCUMENTS

| | | | |
|---|---|---|---|
| 3,137,730 A | 6/1964 | Fitz-William | |
| 3,270,059 A | 8/1966 | Winderl et al. | |
| 4,111,840 A | 9/1978 | Best | |
| 4,701,434 A | 10/1987 | Köll | |
| 4,806,690 A * | 2/1989 | Bowman | B01J 23/75 564/480 |
| 4,855,505 A | 8/1989 | Köll | |
| 5,958,825 A * | 9/1999 | Wulff-Doring | B01J 23/8926 502/300 |
| 6,525,222 B2 | 2/2003 | Nouwen et al. | |
| 7,405,327 B2 | 7/2008 | Haese et al. | |
| 7,700,806 B2 | 4/2010 | van Cauwenberge et al. | |
| 7,919,655 B2 | 4/2011 | Kubanek et al. | |
| 8,063,252 B2 | 11/2011 | Kubanek et al. | |
| 8,268,995 B2 | 9/2012 | Kubanek et al. | |
| 8,293,945 B2 | 10/2012 | Kubanek et al. | |
| 8,318,982 B2 | 11/2012 | Kubanek et al. | |
| 8,324,430 B2 | 12/2012 | Kubanek et al. | |
| 8,487,135 B2 | 7/2013 | Kubanek et al. | |
| 9,019,075 B2 | 4/2015 | Hayashida | |
| 9,174,201 B2 | 11/2015 | Ernst et al. | |
| 2020/0102262 A1* | 4/2020 | Bebensee | C07C 213/02 |

FOREIGN PATENT DOCUMENTS

| | | | |
|---|---|---|---|
| CN | 102190588 A | 9/2011 | |
| CN | 102233272 A | 11/2011 | |
| DE | 1172268 B | 6/1964 | |
| EP | 198699 A2 | 10/1986 | |
| EP | 0839575 A2 | 5/1998 | |
| EP | 1106600 A2 | 6/2001 | |
| EP | 2780109 A1 * | 9/2014 | C07C 229/76 |
| WO | WO-96/38226 A1 | 12/1996 | |
| WO | WO-2005110969 A1 | 11/2005 | |
| WO | WO-2007093514 A1 | 8/2007 | |
| WO | WO-2008006749 A1 | 1/2008 | |

(Continued)

OTHER PUBLICATIONS

U.S. Appl. No. 16/620,023, filed Dec. 2019, Bebensee; Regine Helga.*
U.S. Appl. No. 16/619,987, filed Dec. 6, 2019.
U.S. Appl. No. 16/620,023, filed Dec. 6, 2019.
"Handbook of Heterogeneous Catalysis", ed. Ertl, et al., 1997, pp. 98-101.
Carl Von Ossietzky, "Reaktionskinetische Untersuchungen zur metallkatalysierten Aminierung von Ethylenglykol in der flüssigen Phase", University of Oldenburg, Mar. 17, 2000, 89 pages.
European Search Report for EP Patent Application No. 17175136.5, dated Aug. 2, 2017, 3 pages.
International Preliminary Examination Report for PCT/EP2018/063589 dated May 22, 2019.
International Preliminary Examination Report for PCT/EP2018/063591 dated Aug. 28, 2019.

(Continued)

*Primary Examiner* — Yong L Chu
(74) *Attorney, Agent, or Firm* — Faegre Drinker Biddle & Reath LLP

(57) ABSTRACT

The present invention relates to a process for preparing alkanolamines and/or ethyleneamines in the liquid phase, by reacting ethylene glycol and/or monoethanolamine with ammonia in the presence of an amination catalyst comprising Co, Ru and Sn.

21 Claims, No Drawings

(56) References Cited

FOREIGN PATENT DOCUMENTS

| | | |
|---|---|---|
| WO | WO-2008006750 A1 | 1/2008 |
| WO | WO-2009/008051 A1 | 1/2009 |
| WO | WO-2009080506 A1 | 7/2009 |
| WO | WO-2009080508 A1 | 7/2009 |
| WO | WO-2009080510 A1 | 7/2009 |
| WO | WO-2010031719 A1 | 3/2010 |
| WO | WO-2011067199 A1 | 6/2011 |
| WO | WO-2011067200 A1 | 6/2011 |
| WO | WO-2013072289 A1 | 5/2013 |

OTHER PUBLICATIONS

International Preliminary Examination Report for PCT/EP2018/063613 dated Aug. 28, 2019.
International Search Report for PCT/EP2018/063589 dated Oct. 8, 2018.
International Search Report for PCT/EP2018/063591 dated Aug. 8, 2018.
International Search Report for PCT/EP2018/063613 dated Aug. 8, 2018.

* cited by examiner

METHOD FOR THE PRODUCTION OF ETHYLENEAMINES

CROSS-REFERENCE TO RELATED APPLICATIONS

This application is a national stage application (under 35 U.S.C. § 371) of PCT/EP2018/063591, filed May 24, 2018, which claims benefit of European Application No. 17175136.5, filed Jun. 9, 2017, both of which are incorporated herein by reference in their entirety.

The present invention relates to a process for preparing alkanolamines and ethyleneamines, especially ethylenediamine.

Two processes are generally employed for industrial scale preparation of ethylenediamine (EDA).

Firstly, EDA can be prepared by reaction of 1,2-dichloroethane with ammonia with elimination of HCl (EDC process). A further industrial scale process for preparation of EDA is the reaction of monoethanolamine (MEA) with ammonia in the presence of amination catalysts (MEA process).

As an alternative to the established processes, EDA can also be prepared by reaction of monoethylene glycol (MEG) with ammonia.

Such a process would have various advantages. One advantage is the good availability of MEG compared to MEA.

MEA is prepared on the industrial scale by reaction of ethylene oxide (EO) and ammonia. What is generally formed is a reaction mixture comprising, as well as MEA, also higher ethanolamines such as diethanolamine (DEOA) and triethanolamine (TEOA). These by-products have to be separated from MEA by a separate distillation step. Ethylene oxide is a highly flammable gas that can form explosive mixtures with air. The handling of EO is correspondingly complex. The preparation of MEA thus requires a technically complex EO plant with downstream purifying distillation.

By contrast, MEG can be produced either on the basis of petrochemical raw materials or on the basis of renewable raw materials. By petrochemical means, MEG is likewise prepared from EO by reaction with water. In the same way as in the reaction of EO with ammonia, it is not possible in the reaction of EO with water to prevent MEG that has already formed from reacting with EO to give by-products such as di- and triethylene glycol. The selectivity for MEG is about 90% and is thus, however, distinctly higher than the selectivity for MEA, which is generally 70-80%. The Shell omega process once again distinctly increased the selectivity for MEG—to about 99%. In the omega process, EO is reacted with $CO_2$ to give ethylene carbonate which, in the second step, is selectively hydrolyzed to MEG.

MEG can also be prepared via the synthesis gas route, for example by oxidative carbonylation of methanol to give dimethyl oxalate and subsequent hydrogenation thereof. Thus, a further possible petrochemical raw material for the preparation of MEG is also natural gas or coal. Alternatively, MEG can also be prepared from renewable raw materials, such as corn or sugarcane, by fermentation to ethanol, followed by dehydration to ethene and subsequent reaction with oxygen to give ethylene oxide.

Owing to the many production variants, the availability of MEG is generally high, which generally has a positive effect on raw material costs.

The prior art discloses that the reaction of MEG with ammonia to give EDA can be effected either in the liquid phase or in the gas phase.

The amination of MEG in the gas phase is disclosed in the two Chinese applications CN 102 190 588 and CN 102 233 272.

For instance, CN 102 190 588 describes the one-stage conversion of MEG and ammonia in the presence of Cu catalysts. According to the description, the reaction pressure is within a range from 3 to 30 bar. The reaction temperature is in the range from 150 to 350° C.

Application CN 102 233 272 discloses the reaction of MEG with ammonia in the gas phase over catalysts that include Cu and Ni as main constituents and Zr, Zn, Al, Ti, Mn and Ce as secondary component. However, the composition of the reaction mixtures obtained was not disclosed.

As an alternative to conversion in the gas phase, the reaction of MEG with ammonia and hydrogen can also be effected in the liquid phase. However, there is generally a considerable difference in the reaction characteristics of catalysts in the gas phase and liquid phase, and so it is generally impermissible to apply conclusions from the reaction characteristics of MEG in the gas phase to the reaction characteristics of MEG in the liquid phase.

An overview of the metal-catalyzed amination of MEG in the liquid phase is given in the Diplom thesis "Reaktionskinetische Untersuchungen zur metallkatalysierten Aminierung von Ethylenglykol in der flüssigen Phase" [Studies of Reaction Kinetics of the Metal-Catalyzed Amination of Ethylene Glycol in the Liquid Phase] by Carsten Wolfgang Ihmels ("Reaktionskinetische Untersuchungen zur metallkatalysierten Aminierung von Ethylenglykol in der flüssigen Phase", Diplom thesis from the Carl von Ossietzky University of Oldenburg dated Mar. 17, 2000). Ihmels describes a multitude of further reactions and side reactions that can occur in the amination of MEG, for example the formation of di- and triethanolamine, disproportionation, nitrile formation, carbonyl condensation and fragmentation reactions.

Condensation and disproportionation in the case of dihydric alcohols can ultimately also lead to the formation of oligomers, such as diethylenetriamine (DETA), triethylenetetramine (TETA) and polymers. An important further side reaction is cyclization. For instance, diethanolamine or DETA can react further to give piperazine (PIP). Higher temperatures promote dehydrogenation, which follows on from the cyclization, to give aromatics. Thus, the reaction of MEG with ammonia gives a broad product spectrum, some products in the product spectrum being of greater commercial interest than others. For instance, the commercial demand for EDA, DETA and TETA is higher than that for PIP or aminoethylethanolamine (AEEA). The object of many studies in the reaction of MEG with ammonia was therefore to find catalysts and reaction conditions that lead to an advantageous product spectrum.

Ihmels himself studied the conversion of MEG over supported cobalt/silicon dioxide catalysts. Amination to give the desired MEA and EDA target product was unsuccessful. Instead, high-polymeric reaction products were formed. Under milder conditions, still with incomplete conversion of MEG, the target products MEA and EDA were obtained in low yields. The main products were oligomeric compounds.

U.S. Pat. No. 4,111,840 discloses the reaction of MEG with ammonia and hydrogen at pressures of 500 to 5000 psig (about 34 to 340 bar) over supported Ni/Re catalysts. Supported silica/alumina catalysts having a surface area of 60 $m^2/g$ led to better results here than supported silica/alumina catalysts having a specific surface area of 150 $m^2/g$.

U.S. Pat. No. 3,137,730 discloses the reaction of MEG with ammonia in the liquid phase at temperatures of 200-300° C. and pressures above 1000 psig (about 69 bar) over Cu/Ni catalysts.

DE 1 172 268 discloses the conversion of ethylene glycol over catalysts comprising at least one of the metals Cu, Ag, Mn, Fe, Ni and Co. In one example, MEG was reacted with ammonia at 180° C. and a pressure of 300 bar in the presence of hydrogen over a Co catalyst.

WO 2007/093514 discloses a two-stage process for preparing EDA, wherein, in the first process stage, the amination is conducted over a hydroamination catalyst up to an MEA conversion of not more than 40% and, in the second process stage, a supported shaped Ru/Co catalyst body having small geometry is used and the second stage is conducted at a temperature at least 10° C. higher than the first process stage.

WO 2013072289 discloses the reaction of alcohols with a nitrogen compound over catalysts that include the element Sn in addition to Al, Cu, Ni and Co. Preferred alcohols mentioned are ethylene glycol and monoethanolamine.

Catalysts for the amination of alcohols that comprise Sn are likewise disclosed in WO 2011067200. The catalysts described therein comprise not only Sn but also the elements Co, Ni, Al and Cu.

Further catalysts for the amination of alcohols are disclosed in WO 200908051, WO 2009080508, WO 200006749 and WO 20008006750. The catalysts comprise not only Zr and Ni but also Cu, Sn, Co and/or Fe. Further constituents are elements such as V, Nb, S, O, La, B, W, Pb, Sb, Bi and In.

WO 9/38226 discloses catalysts for the amination of alcohols that comprise Re, Ni, Co, B, Cu and/or Ru. In one example, a support of SiO2 is impregnated with a solution of NH4ReO4, Ni nitrate, H3BO3, Co nitrate and Cu nitrate and then calcined. In a further impregnation step, the calcined and impregnated support is impregnated with Ru chloride.

In U.S. Pat. No. 4,855,505 is the amination of MEG and MEA in the presence of catalysts comprising Ni and/or Co and Ru. This involves contacting a catalyst precursor comprising Ni oxide and/or Co oxide with an Ru halide, for example Ru chloride, and then reducing it in a hydrogen stream.

EP 0839 575 discloses catalysts comprising Co, Ni and mixtures thereof and Ru on a porous metal oxide support. The catalysts are prepared by impregnating the support with the metals, drying and calcining the impregnated support and reducing the calcined support in a hydrogen stream. It is further disclosed that the support can be impregnated with metal compounds in any sequence. In one example, a support is first impregnated with a solution of Ni nitrates, Co nitrates and Cu nitrates, then calcined and further impregnated with an aqueous Ru nitrate solution.

It was an object of the present invention to develop a heterogeneous catalyst for the amination of MEG in the liquid phase that shows adequate activity and selectivity in the conversion of MEG to MEA and/or EDA.

More particularly, the formation of products of value, i.e. those ethanolamines or ethyleneamines with a high commercial significance, especially MEA and EDA, was to be promoted and the formation of cyclic ethyleneamines, especially PIP, and higher ethanolamines, especially AEEA, was to be kept low since the commercial demand for PIP or AEEA is lower than for EDA and MEA.

More particularly, the concentration of particular unwanted by-products, such as NMEDA, NEEDA and ethylamine (EA), was also to be reduced. NMEDA has a volatility that barely differs from EDA, and so the two components are separable only with high separation complexity. It would thus be advantageous if only small amounts of NMEDA were to be formed even in the production. The customary product specifications of EDA require that less than 500 ppm of NMEDA be present in EDA.

In addition, the catalysts were also to have high activity and enable high MEG conversion in order to achieve a good space-time yield.

Overall, a good spectrum of properties in relation to overall selectivity, selectivity quotient and the formation of unwanted by-products was thus to be achieved.

The object of the present invention was achieved by a process for preparing alkanolamines and ethyleneamines in the liquid phase, by reacting ethylene glycol and/or monoethanolamine with ammonia in the presence of an amination catalyst comprising Co, Ru and Sn.

It has been found that, surprisingly, the conversion of MEG and $NH_3$ over amination catalysts that comprise the continuation of Co, Ru and Sn proceeds with high selectivity and the formation of undesirable by-products is reduced.

Moreover, it has been found that the amination catalysts comprise Co, Ru and Sn have a high activity for the conversion of MEG and hence enable high space-time yields in the conversion.

The following abbreviations are used above and hereinafter:
AEEA: aminoethylethanolamine
AEP: aminoethylpiperazine
DETA: diethylenetriamine
EA: ethylamine
EDA: ethylenediamine
EO: ethylene oxide
HEP: hydroxyethylpiperazine
NEEDA: N-ethylethylenediamine
NMEDA: N-methylethylenediamine
MEA: monoethanolamine
MEG: monoethylene glycol
ylPIP: piperazine
TEPA: tetraethylenepentamine
TETA: triethylenetetramine Amination Catalysts The process of the invention for preparing alkanolamines and ethyleneamines by reaction of MEG and/or MEA with $NH_3$ is effected in the presence of amination catalysts, which comprise a continuation of Sn, Co and Ru.

Catalyst Precursors

The amination catalysts are preferably obtained by reduction of catalyst precursors.

Active Composition

The catalyst precursors used comprise an active composition.

The active composition of the catalyst precursors comprises the active metals Co, Ru and Sn and optionally one or more added catalyst elements, and also optionally one or more support materials.

Active Metals

According to the invention, the active composition of the catalyst precursors used in the process of the invention comprises the combination of the active metals Sn, Co and Ru.

Added Catalyst Elements

The active composition of the catalyst precursors used in the process of the invention may optionally comprise one or more added catalyst elements.

The added catalyst elements are metals or semimetals selected from groups 1 to 7, 8 (excluding Ru), 9 (excluding Co), 10 to 13, 14 (excluding Sn) and 15 to 17 of the Periodic Table, the element P and the rare earth metals.

Preferred added catalyst elements are Cu, Ni, Zr, Al, Fe, Pb, Bi, Ce, Y, and Mn.

Particularly preferred added catalyst elements are Cu, Ni, Fe, Zr, Al, Y and Mn.

Very particularly preferred added catalyst elements are Cu, Ni, Fe, Zr and Al.

Very particularly preferred added catalyst elements are Cu, Ni, Zr and Al

Catalytically Active Components

In the catalyst precursor, the active metals and the added catalyst elements are generally in the form of their oxygen compounds, for example of carbonates, oxides, mixed oxides or hydroxides of the added catalyst elements or active metals.

The oxygen compounds of the active metals and of the added catalyst elements are referred to hereinafter as catalytically active components.

However, the term "catalytically active components" is not intended to imply that these compounds are already catalytically active per se. The catalytically active components generally have catalytic activity in the inventive conversion only after reduction of the catalyst precursor.

In general, the catalytically active components are converted to the catalytically active components by a calcination from soluble compounds of the active metals or of the added catalyst elements or precipitates of the active metals or of the added catalyst elements, the conversion generally being effected by dewatering and/or decomposition.

Support Materials

The catalytically active composition may further comprise one or more support materials.

The support materials are generally added catalyst elements which are used in solid form in the preparation of the catalyst precursors and onto which the soluble compounds of the active metals and/or added catalyst elements are precipitated or which are impregnated with the soluble compounds of the active metals or added catalyst elements. In general, support materials are solids having a high surface area.

Preference is given to using support materials that already have the preferred shape and geometry described hereinafter (see section "Shape and geometry of the support materials and catalyst precursors").

The catalytically active components can be applied to the support material, for example as described hereinafter by precipitative application of the active metals or of the added catalyst elements in the form of their sparingly soluble compounds, for example the carbonates, hydrogencarbonates or hydroxides, or by impregnating the support material with soluble compounds of the active metals or added catalyst elements.

The support material used may be the added catalyst element carbon, for example in the form of graphite, carbon black and/or activated carbon.

Preferred support materials are oxides of the added catalyst elements Al, Ti, Zn, Zr and Si or mixtures thereof, for example aluminum oxide (gamma, delta, theta, alpha, kappa, chi or mixtures thereof), titanium dioxide (anatase, rutile, brookite or mixtures thereof), zinc oxide, zirconium dioxide, silicon dioxide (such as silica, fumed silica, silica gel or silicates), aluminosilicates, minerals, such as hydrotalcite, chrysotile and sepiolite.

Particularly preferred support materials are aluminum oxide or zirconium oxide or mixtures thereof.

In a particularly preferred embodiment, the support material is aluminum oxide, zinc oxide or a mixture thereof with a median diameter of the particles $d_{50}$ in the range from 50 to 2000 µm, preferably 100 to 1000 µm and more preferably 300 to 700 µm. In a particularly preferred embodiment, the median diameter $d_{50}$ of the particles is in the range from 1 to 500 µm, preferably 3 to 400 µm and more preferably 5 to 300 µm. In the preferred working examples, the standard deviation of the particle diameter is generally in the range from 5% to 200%, preferably 10% to 100% and especially preferably 20% to 80% of the median diameter $d_{50}$.

Preparation of the Catalyst Precursors

Catalyst precursors can be prepared by known processes, for example by precipitation reactions (e.g. coprecipitation or precipitative application) or impregnation.

Precipitation Reactions-Coprecipitation

Catalyst precursors can be prepared via a coprecipitation of soluble compounds of the active metals or added catalyst elements with a precipitant. For this purpose, one or more soluble compounds of the corresponding active metals and optionally one or more soluble compounds of the added catalyst elements in a liquid is admixed with a precipitant while heating and stirring until the precipitation is complete.

The liquid used is generally water.

Useful soluble compounds of the active metals typically include the corresponding metal salts, such as the nitrates or nitrosylnitrates, acetates, chlorides, sulfates, carboxylates, especially the acetates or nitrates or nitrosylnitrates, particularly preferably the nitrates or nitrosylnitrates, of the aforementioned metals.

The soluble compounds of the added catalyst elements that are used are generally water-soluble compounds of the added catalyst elements, for example the water-soluble nitrates or nitrosylnitrates, chlorides, sulfates, carboxylates, especially the acetate or nitrates or nitrosylnitrates, preferably the nitrates or nitrosylnitrates.

Precipitation Reactions-Precipitative Application

Catalyst precursors can also be prepared by precipitative application.

Precipitative application is understood to mean a preparation method in which one or more support materials are suspended in a liquid and then soluble compounds of the active metals, such as soluble metal salts of the active metals, and optionally soluble compounds of the added catalyst elements are added, and these are then applied by precipitative application to the suspended support material by addition of a precipitant (described, for example, in EP-A2-1 106 600, page 4, and A. B. Stiles, Catalyst Manufacture, Marcel Dekker, Inc., 1983, page 15). The soluble compounds of the active metals or added catalyst elements that are used are generally water-soluble compounds of the active metals or added catalyst elements, for example the water-soluble nitrates or nitrosylnitrates, acetates, chlorides, sulfates, carboxylates, especially the acetates or nitrates or nitrosylnitrates, preferably the nitrates or nitrosylnitrates. The support materials that are used in the precipitative application may be used, for example, in the form of spall, powders or shaped bodies, such as strands, tablets, spheres or rings. Preference is given to using support materials that already have the preferred shape and geometry of the shaped bodies described hereinafter (see section "Shape and geometry of the support materials and catalyst precursors").

The liquid used, in which the support material is suspended, is typically water.

Precipitation Reactions—General

Typically, in the precipitation reactions, the soluble compounds of the active metals or added catalyst elements are precipitated as sparingly soluble or insoluble, basic salts by addition of a precipitant.

The precipitants used are preferably alkalis, especially mineral bases, such as alkali metal bases. Examples of precipitants are sodium carbonate, sodium hydroxide, potassium carbonate or potassium hydroxide.

The precipitants used may also be ammonium salts, for example ammonium halides, ammonium carbonate, ammonium hydroxide or ammonium carboxylates.

The precipitation reactions can be conducted, for example, at temperatures of 20 to 100° C., particularly 30 to 90° C., especially at 50 to 70° C.

The precipitates obtained in the precipitation reactions are generally chemically inhomogeneous and generally comprise mixtures of the oxides, oxide hydrates, hydroxides, carbonates and/or hydrogencarbonates of the metals or semimetals used. With regard to the filterability of the precipitates, it may prove to be favorable for them to be aged—meaning that they are left to themselves for a certain time after precipitation, optionally under hot conditions or with air being passed through.

Impregnation:

The catalyst precursors can also be prepared by impregnating support materials with soluble compounds of the active metals or added catalyst elements (impregnation).

The support materials that are used in the impregnation may be used, for example, in the form of spall, powders or shaped bodies, such as strands, tablets, spheres or rings. Preference is given to using support materials that already have the preferred shape and geometry of the shaped bodies described hereinafter (see section "Shape and geometry of the support materials and catalyst precursors").

The abovementioned support materials can be impregnated by the customary processes (A. B. Stiles, Catalyst Manufacture—Laboratory and Commercial Preparations, Marcel Dekker, New York, 1983), for example by applying a salt of the active metals or added catalyst elements in one or more impregnation stages.

Useful salts of the active metals or of the added catalyst elements generally include water-soluble salts such as the carbonates, nitrates or nitrosylnitrates, acetates, carboxylates, especially the nitrates or nitrosylnitrates, acetates and preferably the nitrates or nitrosylnitrates, of the corresponding active metals or added catalyst elements, which are generally converted at least partly to the corresponding oxides or mixed oxides under the conditions of the calcination. The impregnation can also be effected by the "incipient wetness method", in which the support material is moistened with the impregnation solution up to a maximum of saturation, according to its water absorption capacity, or the support material is sprayed with the impregnation solution. Alternatively, impregnation may take place in supernatant solution.

In the case of multistage impregnation processes, it is appropriate to dry and optionally to calcine between individual impregnation steps. Multistage impregnation should be employed advantageously when the support material is to be contacted with salts in a relatively large amount.

For application of multiple active metals and/or added catalyst elements and/or basic elements to the support material, the impregnation can be effected simultaneously with all salts or in any sequence of the individual salts in succession.

Combination of Various Catalyst Precursor Preparation Processes

In the preparation of the catalyst precursors, it is also possible to combine various preparation methods for the catalyst precursors with one another.

For example, catalyst precursors can be prepared by coprecipitation or precipitative application and impregnated in a further step.

In a preferred embodiment, a catalyst precursor comprising only a portion of the active metals Ru, Co and Sn is prepared by coprecipitation or precipitative application and the missing active metals or the missing portion of the active metals can be applied to the catalyst precursor in a subsequent impregnation step.

Combination of Catalyst Preparation Processes with a Subsequent Impregnation

In a particularly preferred embodiment, a catalyst precursor comprising the active metals Co and Sn is first prepared and is then contacted in a further impregnation step with the active metals Co and Ru.

More preferably, a catalyst precursor is first prepared by precipitation or coprecipitation of the soluble compounds of Co and Sn onto a support material and the catalyst precursor thus obtained is contacted in a further step with a soluble compound of Ru and a soluble compound of Co.

The Ru content of the solutions with which the catalyst precursor is contacted is typically in the range from 0.1% to 50% by weight, preferably 1% to 40% by weight and more preferably 2% to 15% by weight.

The Co content of the solutions with which the catalyst precursor is contacted is typically in the range from 0.1% to 20% by weight, preferably 0.1% to 5% by weight and more preferably 0.15% to 2% by weight.

The catalyst precursor is generally contacted with a soluble Ru compound or a soluble Co compound after an oxidative or inert calcination of the catalyst precursor, preferably an oxidative calcination, or, if a shaping step is effected, after the heat treatment following the shaping step and prior to the reduction of the catalyst precursor.

The catalyst precursor can be contacted simultaneously or subsequently with a soluble Ru compound and a soluble Co compound.

In a preferred embodiment, the catalyst precursor is contacted with a solution comprising both a soluble compound of Ru and a soluble compound of Co.

In a further preferred embodiment, the catalyst precursor is contacted in a first stage with a solution comprising a soluble compound of Ru and subsequently in a second stage with a solution comprising a soluble compound of Co.

In a further preferred embodiment, the catalyst precursor is contacted in a first stage with a solution comprising a soluble compound of Co and subsequently in a second stage with a solution comprising a soluble compound of Ru.

In the case of multistage impregnation processes, between the individual impregnation steps, the catalyst precursor can be separated from the impregnation solution, as described hereinafter, and dried and optionally calcined.

If the contacting is effected with a soluble Ru compound and a soluble Co compound in two or more impregnation steps, it is preferable that the second impregnation directly follows the drying step of the first impregnation step without a calcination after the drying step between the first and second impregnation.

After the last drying step, the catalyst precursor is generally calcined, in which case, in a particularly preferred embodiment, the calcination is performed as a reductive calcination and the reductively calcined catalyst precursor is passivated thereafter, as described below.

Combination of Precipitative Application and Subsequent Impregnation

In a particularly preferred embodiment, a catalyst precursor comprising the active metals Co and Sn is prepared by precipitative application to the support material and, in a further impregnation step, contacted simultaneously or subsequently with Co and Ru.

Most preferably, soluble compounds of Co and Sn are precipitated onto a finely dispersed support material, where the soluble compound is Sn nitrate and the precipitative application is effected in the presence of a complexing agent.

The soluble compound of Co is preferably Co nitrate.

The precipitative application is further preferably effected in the presence of at least one further soluble compound of an added catalyst element, preferably of a soluble compound of Cu and/or Ni. Further preferably, the added catalyst elements are likewise used in the form of their nitrates or nitrosylnitrates.

The complexing agent is preferably selected from the group consisting of glycolic acid, lactic acid, hydracrylic acid, hydroxybutyric acid, hydroxyvaleric acid, malic acid, mandelic acid, citric acid, sugar acids, tartronic acid, tartaric acid, oxalic acid, malonic acid, maleic acid, succinic acid, glutaric acid, adipic acid, glycine, hippuric acid, EDTA, alanine, valine, leucine or isoleucine.

The support material is preferably aluminum oxide or zirconium oxide or a mixture thereof.

The median diameter $d_{50}$ of the particles of the support material used is preferably in the range from 1 to 500 µm, preferably 3 to 400 µm and more preferably 5 to 300 µm.

The standard deviation of the particle diameter is generally in the range from 5% to 200%, preferably 10% to 100% and especially preferably 20% to 80% of the median diameter $d_{50}$. After the precipitative application, the catalyst precursor is generally worked up as described below, by separating catalyst precursors from the solution from which the precipitative application was effected, and washing, drying, calcining and optionally converting to the desired shape in a shaping step.

Preferably, the calcining is followed by a shaping step in which the catalyst precursor is processed to give shaped bodies, especially tablets.

The height of the tablets is preferably in the range from 1 to 10 and more preferably in the range from 1.5 to 3 mm. The ratio of height h of the tablet to the diameter D of the tablet is preferably 1:1 to 1:5, more preferably 1:1 to 2.5 and most preferably 1:1 to 1:2.

The shaping step is followed, as described above, by the contacting of the catalyst precursor with a soluble compound of Ru and a soluble compound of Co.

However, it is also possible that the calcination is not followed by a shaping step and the catalyst precursor obtained after the precipitative application, as described above, is contacted with a soluble compound of Ru and a soluble compound of Co without a shaping step.

After the contacting with Ru and Co, the catalyst precursor is preferably removed and dried as described above.

More preferably, the drying is followed by a reductive calcination which is preferably performed as described above.

Workup of the Catalyst Precursors

The impregnated catalyst precursors obtained by these impregnation methods or the precipitates obtained by the precipitation methods are typically processed by separating them from the liquid in which the impregnation or precipitation has been conducted, and washing, drying, calcining and optionally conditioning and subjecting them to a shaping process.

Separation and Washing

The impregnated catalyst precursors or the precipitates obtained after the precipitation process are generally separated from the liquid in which the catalyst precursors were prepared and washed.

Processes for separating and washing the catalyst precursors are known, for example, from the article "Heterogenous Catalysis and Solid Catalysts, 2. Development and Types of Solid Catalysts", in Ullmann's Encyclopedia of Industrial Chemistry (DOI: 10.1002/14356007.005_002).

The wash liquid used is generally a liquid in which the separated catalyst precursor is sparingly soluble but which is a good solvent for impurities adhering to the catalyst, for example precipitant. A preferred wash liquid is water.

In batch preparation, the separation is generally effected with frame filter presses. The washing of the filter residue with wash liquid can be effected here by passing the wash liquid in countercurrent direction to the filtration direction.

In continuous preparation, the separation is generally effected with rotary drum vacuum filters. The washing of the filter residue is typically effected by spraying the filter residue with the wash liquid.

The catalyst precursor can also be separated off by centrifugation. In general, the washing here is effected by adding wash liquid in the course of centrifuging.

Drying

The catalyst precursor separated off is generally dried.

Processes for drying the catalyst precursors are known, for example, from the article "Heterogenous Catalysis and Solid Catalysts, 2. Development and Types of Solid Catalysts", in Ullmann's Encyclopedia of Industrial Chemistry (D0110.1002/14356007.005_002).

The drying is effected here at temperatures in the range from preferably 60 to 200° C., especially from 80 to 160° C. and more preferably from 100 to 140° C., where the drying time is preferably 6 h or more, for example in the range from 6 to 24 h. However, depending on the moisture content of the material to be dried, shorter drying times, for example about 1, 2, 3, 4 or 5 h, are also possible.

The washed catalyst precursor that has been separated off can be dried, for example, in chamber ovens, drum driers, rotary kilns or belt driers.

The catalyst precursors can also be dried by spray-drying a suspension of the catalyst precursor.

Calcination

In general, the catalyst precursors are calcined after the drying.

During the calcination, thermally labile compounds of the active metals or added catalyst elements, such as carbonates, hydrogencarbonates, nitrates or nitrosylnitrates, chlorides, carboxylates, oxide hydrates or hydroxides, are at least partly converted to the corresponding oxides and/or mixed oxides.

The calcination is generally effected at a temperature in the range from 250 to 1200° C., preferably 300 to 1100° C. and especially from 500 to 1000° C.

The calcination can be effected under any suitable gas atmosphere.

In a preferred embodiment, the calcination is conducted as what is called an inert calcination. In inert calcination, the calcination is effected in the presence of inert gases in the very substantial absence of oxidizing gases, especially oxygen, and in the very substantial absence of reducing gases, especially hydrogen. Preferred inert gases are nitrogen, helium, neon, argon, carbon dioxide or mixtures thereof, especially nitrogen or argon.

In a preferred embodiment, the calcination is effected as what is called an oxidative calcination in the presence of an oxidizing gas. The oxidizing gas used is preferably oxygen, preference being given especially to air or air mixtures, such as lean air.

In a preferred embodiment, air is used together with nitrogen, where the proportion by volume of air is preferably in the range from 20% to 100%, more preferably 35% to 90% and especially preferably 30% to 70% by volume.

In a very particularly preferred embodiment, the calcination is conducted as what is called a reductive calcination. In this case, the calcination is conducted in the presence of a reducing gas, especially hydrogen.

In addition, the reductive calcination can be conducted in the presence of an inert gas, preferably nitrogen, helium or argon, where the proportion by volume of reducing gas, especially hydrogen, in mixtures with inert gas is preferably in the range from 20% to 100% by weight, more preferably in the range from 35% to 90% by weight and most preferably in the range from 30% to 70% by weight.

It is additionally preferable to increase the proportion of hydrogen in the mixture with inert gas gradually or stepwise, for example from 0% by volume of hydrogen to 50% by volume of hydrogen. For instance, in the course of heating, the proportion of volume of hydrogen may be 0% by volume and, on attainment of the calcination temperature, may be increased in one or more stages or gradually to 50% by volume.

The temperature in the reductive calcination is preferably 100 to 400° C., more preferably 150 to 350° C. and more preferably 200 to 300° C.

The reductive calcination is generally followed by a passivation, for example as described hereinafter.

The calcination is generally effected in a muffle furnace, a rotary kiln and/or a tunnel kiln, the calcination time preferably being 1 h or more, more preferably in the range from 1 to 24 h and most preferably in the range from 2 to 12 h.

Shape and Geometry of the Support Materials or Catalyst Precursors

The catalyst precursors or the support material are preferably used in the form of powder or spall or in the form of shaped bodies.

If the catalyst precursor is used in the form of powder or spall, the median diameter of the particles $d_{50}$ is generally in the range from 50 to 2000 µm, preferably 100 to 1000 µm and more preferably 300 to 700 µm. The standard deviation of the particle diameter is generally in the range from 5% to 200%, preferably 10% to 100% and especially preferably 20% to 80% of the median diameter $d_{50}$.

In a particularly preferred embodiment, the median diameter $d_{50}$ of the particles of the powder or spall used is in the range from 1 to 500 µm, preferably 3 to 400 µm and more preferably 5 to 300 µm. The standard deviation of the particle diameter is generally in the range from 5% to 200%, preferably 10% to 100% and especially preferably 20% to 80% of the median diameter $d_{50}$.

However, the support materials or catalyst precursors can also preferably be used in the form of shaped bodies in the process of the invention.

Suitable shaped bodies are shaped bodies having any geometry or shape. Preferred shapes are tablets, rings, cylinders, star extrudates, wagonwheels or spheres, particular preference being given to tablets, rings, cylinders, spheres or star extrudates. Very particular preference is given to the cylinder shape.

In the case of spheres, the diameter of the sphere shape is preferably 20 mm or less, more preferably 10 mm or less, even more preferably 5 mm or less and especially preferably 3 mm or less.

In a preferred embodiment, in the case of spheres, the diameter of the sphere shape is preferably in the range from 0.1 to 20, more preferably 0.5 to 10 mm, even more preferably 1 to 5 mm and especially preferably 1.5 to 3 mm.

In the case of strands or cylinders, the ratio of length:diameter is preferably in the range from 1:1 to 20:1, more preferably 1:1 to 14:1, even more preferably in the range from 1:1 to 10:1 and especially preferably in the range from 1:2 to 6:1.

The diameter of the strands or cylinders is preferably 20 mm or less, more preferably 15 mm or less, even more preferably 10 mm or less and especially preferably 3 mm or less.

In a preferred embodiment, the diameter of the strands or cylinders is preferably in the range from 0.5 to 20 mm, more preferably in the range from 1 to 15 mm, most preferably in the range from 1.5 to 10 mm.

In the case of tablets, the height h of the tablet is preferably 20 mm or less, more preferably 10 mm or less, even more preferably 5 mm or less and especially preferably 3 mm or less.

In a preferred embodiment, the height h of the tablet is preferably in the range from 0.1 to 20 mm, more preferably in the range from 0.5 to 15 mm, even more preferably in the range from 1 to 10 mm and especially preferably in the range from 1.5 to 3 mm.

The ratio of height h (or thickness) of the tablet to the diameter D of the tablet is preferably 1:1 to 1:5, more preferably 1:1 to 1:2.5 and most preferably 1:1 to 1:2.

The shaped body used preferably has a bulk density (to EN ISO 6) in the range from 0.1 to 3 kg/l, preferably from 1.0 to 2.5 kg/l and especially preferably 1.2 to 1.8 kg/l.

Shaping

In the case of preparation of the catalyst precursors by impregnation or by precipitative application, preference is given to using support materials that already have the above-described preferred shape and geometry.

Support materials or catalyst precursors that do not have the preferred shape described above can be subjected to a shaping step.

In the course of shaping, the support materials or catalyst precursors are generally conditioned by adjusting them to a particular particle size by grinding.

After the grinding, the conditioned support material or the conditioned catalyst precursor can be mixed with further additives, such as shaping aids, for example graphite, binders, pore formers and pasting agents, and processed further to give shaped bodies. Preferably, the catalyst precursor is mixed only with graphite as shaping aid, and no further additives are added in the course of shaping.

Standard processes for shaping are described, for example, in Ullmann [Ullmann's Encyclopedia Electronic Release 2000, chapter: "Catalysis and Catalysts", pages 28-32] and by Ertl et al. [Ertl, Knözinger, Weitkamp, Handbook of Heterogeneous Catalysis, VCH Weinheim, 1997, pages 98 ff.].

Standard processes for shaping are, for example, extrusion, tableting, i.e. mechanical pressing, or pelletizing, i.e. compaction by circular and/or rotating movements.

The shaping operation can give shaped bodies with the abovementioned geometry.

The shaping can alternatively be effected by spray-drying a suspension of the catalyst precursor.

The conditioning or shaping is generally followed by a heat treatment. The temperatures in the heat treatment typically correspond to the temperatures in the calcination.

Composition of the Catalyst Precursors

Proportion of the Active Composition

The catalyst precursors used in the process are preferably used in the form of catalyst precursors consisting solely of catalytically active composition and optionally a shaping aid (for example graphite or stearic acid) if the catalyst precursor is used in the form of a shaped body.

The proportion of the catalytically active composition, based on the total mass of the catalyst precursor, is typically 70% to 100% by weight, preferably 80% to 100% by weight, more preferably 90% to 100% by weight, even more preferably 95% by weight to 100% by weight and especially preferably 97% by weight to 100% by weight.

Determination of the Composition of the Catalyst Precursors.

The composition of the catalyst precursors can be measured by means of known methods of elemental analysis, for example of atomic absorption spectrometry (AAS), of atomic emission spectrometry (AES), of X-ray fluorescence analysis (XFA) or of ICP-OES (Inductively Coupled Plasma Optical Emission Spectrometry).

The concentration figures (in % by weight) of the catalytically active components in the context of the present invention are reported as the corresponding oxide.

The added catalyst elements of group 1 (alkali metals) are calculated as $M_2O$, for example $Na_2O$.

The added catalyst elements of group 2 (alkaline earth metals) are calculated as MO, for example MgO or CaO.

The added catalyst elements of group 13 (boron group) are calculated $M_2O_3$, for example $B_2O_3$ or $Al_2O_3$.

In the carbon group (group 14), Si is calculated as $SiO_2$, Ge as GeO, Sn as SnO and Pb as PbO.

In the nitrogen group (group 15), P is calculated as $H_3PO_4$, As as $As_2O_3$, Sb as $Sb_2O_3$ and Bi as $Bi_2O_3$.

In the group of the chalcogens (group 16), Se is calculated as $SeO_2$ and Te as $TeO_2$.

In the scandium group (group 3), Sc is calculated as $Sc_2O_3$, Y as $Y_2O_3$ and La as $La_2O_3$.

In the titanium group (group 4), Ti is calculated as $TiO_2$, Zr as $ZrO_2$ and Hf as $HfO_2$.

In the vanadium group (group 5), V is calculated as $V_2O_5$, Nb as $Nb_2O_5$ and Ta as $Ta_2O_5$.

In the chromium group (group 6), Cr is calculated as $CrO_2$, Mo as $MoO_3$ and W as $WO_2$.

In the manganese group (group 7), Mn is calculated as $MnO_2$ and Re as $Re_2O_7$.

In the iron group (group 8), Fe is calculated as $Fe_2O_3$, Ru as $RuO_2$ and Os as $OsO_4$.

In the cobalt group (group 9), Co is calculated as CoO, Rh as $RhO_2$ and Ir as $IrO_2$.

In the nickel group (group 10), Ni is calculated as NiO, Pd as PdO and Pt as PtO.

In the copper group (group 11), Cu is calculated as CuO, Ag as AgO and Au as $Au_2O_3$.

In the zinc group (group 12), Zn is calculated as ZnO, Cd as CdO and Hg as HgO.

The concentration figures (in % by weight) of the catalytically active components of the catalyst precursor are each based—unless stated otherwise—on the total mass of the catalyst precursor after the last calcination thereof or when the last calcination as reductive calcination has been carried out, after the last drying step before the reductive calcination.

Composition of the Catalyst Precursors Depending on the Preparation Method

The composition of the catalyst precursors is generally dependent on the preparation method described hereinafter (coprecipitation or precipitative application or impregnation).

Catalyst precursors that are prepared by coprecipitation do not comprise any support material. If the precipitation, as described hereinafter, is effected in the presence of a support material, the precipitation is referred to in the context of the present invention as precipitative application.

Catalyst precursors that are prepared by coprecipitation comprise the active metals Ru, Co and Sn in the active composition.

In the case of catalyst precursors that are prepared by coprecipitation, the composition of the catalytically active components of the active metals is preferably in the range from 1% to 70% by weight, more preferably 5% to 60% by weight and even more preferably 10% to 50% by weight, based on the total mass of the catalyst precursor, and where the catalytically active components are calculated as the oxide.

Catalyst precursors that are prepared by coprecipitation comprise preferably 1 to 5, more preferably 1 to 4 and especially preferably 1 to 3 different added catalyst elements.

Irrespective of the number of added catalyst elements present in the active composition, in the case of catalyst precursors that are prepared by coprecipitation, the composition of the catalytically active components of the added catalyst elements is preferably in the range from 1% to 95% by weight, more preferably 10% to 90% by weight, most preferably 20% to 85% by weight, and especially preferably 40% to 80% by weight, based on the total mass of the catalyst precursor, and where the catalytically active components are calculated as the oxide.

Catalyst precursors that are prepared by precipitative application comprise generally 5% to 95% by weight, preferably 10% to 75% by weight and more preferably 15% to 50% by weight of support material.

Catalyst precursors that are prepared by coprecipitation comprise the active metals Ru, Co and Sn in the active composition.

In the case of catalyst precursors that are prepared by precipitative application, the composition of the catalytically active components of the active metals is preferably in the range from 1% to 80% by weight, more preferably 5% to 70% by weight and most preferably 10% to 60% by weight, based on the total mass of the catalyst precursor, and where the catalytically active components are calculated as the oxide.

Catalyst precursors that are prepared by precipitative application comprise preferably 1 to 5, more preferably 1 to 4 and especially preferably 1 to 3 different added catalyst elements.

Irrespective of the number of added catalyst elements present in the active composition, in the case of catalyst precursors that are prepared by precipitative application, the composition of the catalytically active components of the added catalyst elements is preferably in the range from 1% to 80% by weight, more preferably 5% to 70% by weight and most preferably 10% to 60% by weight, based on the total mass of the catalyst precursor, and where the catalytically active components are calculated as the oxide.

Catalyst precursors that are prepared by impregnation comprise generally 50% to 99% by weight, preferably 60% to 98% by weight and more preferably 70% to 97% by weight of support material.

Catalyst precursors that are prepared by impregnation comprise the active metals Ru, Co and Sn in the active composition.

In the case of catalyst precursors that are prepared by impregnation, the composition of the catalytically active components of the active metals is preferably in the range from 1% to 50% by weight, more preferably 2% to 40% by weight and most preferably 3% to 30% by weight, based on the total mass of the catalyst precursors, and where the catalytically active components are calculated as the oxide.

Catalyst precursors that are prepared by impregnation comprise preferably 1 to 5, more preferably 1 to 4 and especially preferably 1 to 3 different added catalyst elements.

Irrespective of the number of added catalyst elements present in the active composition, in the case of catalyst precursors that are prepared by impregnation, the composition of the catalytically active components of the added catalyst elements is preferably in the range from 1% to 50% by weight, more preferably 2% to 40% by weight and preferably 3% to 30% by weight, based on the total mass of the catalyst precursors, and where the catalytically active components are calculated as the oxide.

Preferred Catalyst Precursor Compositions

In a preferred embodiment, the catalyst precursor comprises: 0.01% to 20% by weight, more preferably 0.1% to 15% by weight and especially preferably 1% to 10% by weight of catalytically active components of Ru, calculated as $RuO$; and 1% to 50% by weight, more preferably 10% to 45% by weight and especially preferably 20% to 40% by weight of catalytically active components of Co, calculated as $CoO$; and 0.1% to 5% by weight, more preferably 0.2% to 4% by weight and especially preferably 1% to 3% by weight of catalytically active components of Sn, calculated as $SnO$.

In a particularly preferred embodiment, the catalyst precursor comprises:
(i) 0.2% to 5% by weight of catalytically active components of Sn, calculated as $SnO$,
(ii) 1% to 35% by weight of catalytically active components of Co, calculated as $CoO$,
(iii) 10% to 80% by weight of catalytically active components of Al and/or Zr, calculated as $Al_2O_3$ and $ZrO_2$ respectively;
(iv) 1% to 35% by weight of catalytically active components of Cu and/or 1% to 35% by weight of catalytically active components of Ni, calculated as $CuO$ and $NiO$ respectively; and
(v) 0.01% to 20% by weight of catalytically active components of Ru, calculated as $RuO$.

In a particularly preferred embodiment, the catalyst precursor comprises:
(i) 0.2% to 5% by weight of catalytically active components of Sn, calculated as $SnO$,
(ii) 5% to 35% by weight of catalytically active components of Co, calculated as $CoO$,
(iii) 15% to 80% by weight of catalytically active components of Al and/or Zr, calculated as $Al_2O_3$ and $ZrO_2$ respectively;
(iv) 1% to 20% by weight of catalytically active components of Cu, calculated as $CuO$,
(v) 5% to 35% by weight of catalytically active components of Ni, calculated as $NiO$; and
(vi) 0.1% to 20% by weight of catalytically active components of Ru, calculated as $RuO$.

The abovementioned compositions are preferably obtained by, in accordance with the particularly preferred embodiment described above, first preparing a catalyst precursor comprising the active metals Co and Sn by precipitative application to a support material comprising aluminum oxide and/or zirconium oxide, and contacting the catalyst precursor with soluble compounds of Co and Ru in a subsequent impregnation step.

Reduction

According to the invention, MEG and/or MEA and ammonia are converted over a reduced catalyst precursor.

The reduction generally converts the catalyst precursor to its catalytically active form.

In a preferred embodiment, the reduction can be effected by performing the last calcination step as described above as a reductive calcination. The reductive calcination is preferably followed by a passivation of the reductively calcined catalyst for better handling of the catalysts. Prior to the contacting with MEG and/or ammonia, the passivated catalyst is preferably activated as described hereinafter.

If the last calcination step was configured as an inert or oxidative calcination, in a further preferred embodiment, the last calcination step is followed by a separate reduction of the catalyst precursor.

The reducing agent used is typically hydrogen or a hydrogen-comprising gas.

The hydrogen is generally used in technical grade purity. The hydrogen may also be used in the form of a hydrogen-comprising gas, i.e. with additions of other inert gases, such as nitrogen, helium, neon, argon or carbon dioxide. In a preferred embodiment, hydrogen is used together with nitrogen, where the proportion by volume of hydrogen is preferably in the range from 1% to 50%, more preferably 2.5% to 30% and especially preferably 5% to 25% by volume. The hydrogen stream can also be recycled into the reduction as cycle gas, optionally mixed with fresh hydrogen and optionally after removal of water by condensation.

The reduction is preferably effected in an agitated or unagitated reduction furnace.

The catalyst precursor is more preferably reduced in a reactor in which the catalyst precursors are arranged in the form of a fixed bed. More preferably, the catalyst precursor is reduced in the same reactor in which the subsequent reaction of MEG and/or MEA with NH3 is effected. In addition, the catalyst precursor can be reduced in the fluidized bed in a fluidized bed reactor.

The catalyst precursor is generally reduced at reduction temperatures of 50 to 600° C., especially of 100 to 500° C., more preferably of 150 to 450° C.

The partial hydrogen pressure is generally from 1 to 300 bar, especially from 1 to 200 bar, more preferably from 1 to 100 bar, where the pressure figures here and hereinafter are based on the pressure measured in absolute terms.

The duration of the reduction is generally dependent on the size and shape of the reactor and is generally performed only with sufficient speed as to avoid a significant temperature rise in the reactor. This means that, according to the shape and size of the reactor, the reduction can take several hours to several weeks.

During the reduction, a solvent may be supplied in order to remove water of reaction formed and/or in order, for example, to be able to more quickly heat the reactor and/or to be able to better remove heat during the reduction. The solvent may also be supplied here in supercritical form.

Suitable solvents used may be the solvents described above. Preferred solvents are water; ethers such as methyl tert-butyl ether, ethyl tert-butyl ether, dioxane or tetrahydrofuran.

Particular preference is given to water or tetrahydrofuran. Suitable solvents likewise include suitable mixtures.

The catalyst thus obtained can be handled under inert conditions after the reduction. The catalyst can preferably be handled and stored under an inert gas such as nitrogen or under an inert liquid, for example an alcohol, water or the product of the particular reaction for which the catalyst is used. In that case, the catalyst may need to be freed of the inert liquid prior to commencement of the actual reaction.

The storage of the catalyst under inert substances enables uncomplicated and safe handling and storage of the catalyst.

Passivation

After the reduction or the reductive calcination, the catalyst is preferably contacted with an oxygen-comprising gas stream such as air or a mixture of air with nitrogen.

This gives a passivated catalyst. The passivated catalyst generally has a protective oxide layer.

This protective oxide layer simplifies the handling and storage of the catalyst, such that, for example, the installation of the passivated catalyst into the reactor is simplified.

For passivation, the reductive calcination or the reduction step for the reduced catalyst is followed by contacting with an oxygenous gas, preferably air. The oxygenous gas may be used with additions of inert gases, such as nitrogen, helium, neon, argon or carbon dioxide. In a preferred embodiment, air is used together with nitrogen, where the proportion by volume of air is preferably in the range from 1% to 80%, more preferably 20% to 70% and especially preferably 30% to 60% by volume. In a preferred embodiment, the proportion by volume of air in the mixture with nitrogen is increased gradually from 0% to about 50% by volume.

The passivation is effected preferably at temperatures up to 50° C., preferably up to 45° C. and most preferably up to 35° C.

Activation

A passivated catalyst is preferably reduced by treatment of the passivated catalyst with hydrogen or a hydrogen-comprising gas prior to the contacting with the reactants. The activation conditions correspond generally to the reaction conditions that are employed in the reduction of the catalyst precursors obtained by oxidative or inert calcination. The activation generally eliminates the protective passivation layer.

Reactants

According to the invention, the inventive conversion of ethylene glycol (EG) and/or monoethanolamine (MEA) and ammonia ($NH_3$) is effected in the presence of the reduced or activated amination catalysts in the liquid phase.

Ethylene Glycol

As ethylene glycol is preferably industrial ethylene glycol having a purity of at least 98%, and most preferably ethylene glycol having a purity of at least 99% and most preferably of at least 99.5%.

The ethylene glycol used in the process can be prepared from ethylene obtainable from petrochemical processes. For instance, in general, ethene is oxidized in a first stage to ethylene oxide, which is subsequently reacted with water to give ethylene glycol. The ethylene oxide obtained can alternatively be reacted with carbon dioxide in what is called the omega process to give ethylene carbonate, which can then be hydrolyzed with water to give ethylene glycol. The omega process features a higher selectivity for ethylene glycol since fewer by-products, such as di- and triethylene glycol, are formed.

Ethene can alternatively be prepared from renewable raw materials. For instance, ethene can be formed by dehydration from bioethanol.

Ethylene glycol can also be prepared via the synthesis gas route, for example by oxidative carbonylation of methanol to give dimethyl oxalate and subsequent hydrogenation thereof.

Thus, a further possible petrochemical raw material for the preparation of MEG is also natural gas or coal.

MEA

MEA may also be used in the process of the invention.

MEA can, as described above, be prepared by reacting ethylene oxide with ammonia.

Preferably, MEA can be prepared by reacting MEG with ammonia, for example by the process of the invention, by first reacting MEG with ammonia and separating the MEA formed in addition to EDA from EDA and recycling the MEA separated off, optionally together with unconverted MEG, into the preparation process of the invention.

When MEA is used in the process of the invention without MEG, MEA is preferably used with a purity of at least 97%, and most preferably with a purity of at least 98% and most preferably of at least 99%.

When MEA is used together with MEG in the process of the invention, the proportion by weight of MEA in relation to the mass of MEA and MEG is preferably in the range from 0% to 60% by weight, more preferably 10% to 50% by weight and most preferably 20% to 40% by weight.

Ammonia

According to the invention, ethylene glycol and/or monoethanolamine is reacted with ammonia. The ammonia used may be conventional commercially available ammonia, for example ammonia with a content of more than 98% by weight of ammonia, preferably more than 99% by weight of ammonia, preferably more than 99.5% by weight, in particular more than 99.8% by weight of ammonia.

Hydrogen

The process of the invention is preferably effected in the presence of hydrogen.

The hydrogen is generally used in technical grade purity. The hydrogen can also be used in the form of a hydrogen-comprising gas, i.e. with additions of other inert gases, such as nitrogen, helium, neon, argon or carbon dioxide. Hydrogen-comprising gases used may, for example, be reformer offgases, refinery gases etc., if and as long as these gases do not comprise any catalyst poisons for the catalysts used, for example CO. However, preference is given to using pure hydrogen or essentially pure hydrogen in the process, for example hydrogen having a content of more than 99% by weight of hydrogen, preferably more than 99.9% by weight of hydrogen, more preferably more than 99.99% by weight of hydrogen, especially more than 99.999% by weight of hydrogen.

Reaction in the Liquid Phase

According to the invention, ethylene glycol and/or monoethanolamine are reacted with ammonia and an amination catalyst in the liquid phase.

In the context of the present invention, "reaction in the liquid phase" means that the reaction conditions, such as pressure and temperature, are adjusted such that both ethylene glycol and monoethanolamine are present in the liquid phase and flow around the amination catalyst in liquid form.

The reaction of MEG and/or MEA with ammonia can be conducted continuously or batchwise. Preference is given to a continuous reaction.

Reactors

Suitable reactors for the reaction in the liquid phase are generally tubular reactors. The catalyst may be arranged as a moving bed or fixed bed in the tubular reactors.

Particular preference is given to reacting ethylene glycol and/or monoethanolamine with $NH_3$ in a tubular reactor in which the amination catalyst is arranged in the form of a fixed bed.

If the catalyst is arranged in the form of a fixed bed, it may be advantageous, for the selectivity of the reaction, to "dilute", so to speak, the catalyst in the reactor by mixing it with inert random packings. The proportion of the random packings in such catalyst preparations may be 20 to 80, preferably 30 to 60 and more preferably 40 to 50 parts by volume.

Alternatively, the reaction is advantageously effected in a shell and tube reactor or in a single-stream plant. In a single-stream plant, the tubular reactor in which the reaction is effected may consist of a series connection of a plurality of (e.g. two or three) individual tubular reactors. A possible and advantageous option here is the intermediate introduction of feed (comprising the reactant and/or ammonia and/or $H_2$) and/or cycle gas and/or reactor output from a downstream reactor.

Reaction Conditions

When working in the liquid phase, the MEG and/or MEA plus ammonia are guided simultaneously in liquid phase, including hydrogen, over the catalyst, which is typically in a preferably externally heated fixed bed reactor, at pressures of generally 5 to 30 MPa (50-300 mbar), preferably 5 to 25 MPa, more preferably 20 15 to 25 MPa, and temperatures of generally 80 to 350° C., particularly 100 to 300° C., preferably 120 to 270° C., more preferably 130 to 250° C., especially 160 to 230° C.

The partial hydrogen pressure is preferably 0.25 to 20 MPa (2.5 to 200 bar), more preferably 0.5 to 15 MPa (5 to 150 bar), even more preferably 1 to 10 MPa (10 to 100 bar) and especially preferably 2 to 5 MPa (20 to 50 bar).

Input

ME and/or MEA and ammonia are supplied to the reactor preferably in liquid form and contacted in liquid form with the amination catalyst.

Either trickle mode or liquid-phase mode is possible.

It is advantageous to heat the reactants, preferably to the reaction temperature, even before they are supplied to the reaction vessel.

Ammonia is preferably used in 0.90 to 100 times the molar amount, especially in 1.0 to 20 times the molar amount, based in each case on the MEG and/or MEA used.

The catalyst hourly space velocity is generally in the range from 0.05 to 0.5, preferably 0.1 to 2, more preferably 0.2 to 0.6, kg (MEG+MEA) per kg of catalyst and hour.

At the catalyst hourly space velocities stated, the conversion of MEG or MEA is generally in the range from 20% to 75%, preferably in the range from 30% to 60% and most preferably in the range from 35% to 55%.

The water of reaction formed in the course of the reaction, one mole per mole of alcohol group converted in each case, generally has no detrimental effect on the degree of conversion, the reaction rate, the selectivity, or the catalyst lifetime, and is therefore usefully removed from the reaction product—by distillation, for example—only when said product is worked up.

Output

The output from the amination reactor comprises the products of the amination reaction, unconverted reactants, such as ethylene glycol and ammonia, and also hydrogen and water.

As products of the amination reaction, the output from the amination reactor also comprises the corresponding ethanolamines and/or ethyleneamines based on MEG.

The output from the amination reactor preferably comprises MEA and/or EDA.

As products from the amination reaction, the reaction output also preferably comprises higher linear ethyleneamines of the general formula

R—$CH_2$—$CH_2$—$NH_2$ where R is a radical of the formula —(NH—$CH_2$—$CH_2$)$_x$—$NH_2$ where x is an integer in the range from 1 to 4, preferably 1 to 3 and most preferably 1 to 2. Preferably, the reaction output comprises DETA, TETA and TEPA, more preferably DETA and TETA and especially preferably DETA.

As products of the amination reaction, the output from the amination reactor may also comprise higher linear ethanolamines of the formula

R—$CH_2$—$CH_2$—OH where R is a radical of the formula —(NH—$CH_2$—$CH_2$)$_x$—$NH_2$ where x is an integer in the range from 1 to 4, preferably 1 to 3 and most preferably 1 to 2.

One example of a higher linear ethanolamine is AEEA.

As products of the amination reaction, the reaction output may also comprise cyclic ethanolamines of the formula

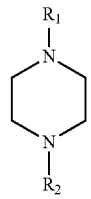

where $R_1$ is a radical of the formula —($CH_2$—$CH_2$—NH)$_x$—$CH_2$—$CH_2$—OH where x is an integer in the range from 0 to 4, preferably 0 to 3 and more preferably 1 to 2, and $R_2$ is independently or simultaneously either H or a radical of the formula —($CH_2$—$CH_2$—NH)$_x$—$CH_2$—$CH_2$—OH where x is an integer in the range from 0 to 4, preferably 0 to 3 and more preferably 1 to 2, or a radical of the formula —($CH_2$—$CH_2$—NH)$_x$—$CH_2$—$CH_2$—$NH_2$ where x is an integer in the range from 0 to 4, preferably 0 to 3 and more preferably 1 to 2. One example of a cyclic ethanolamine is hydroxyethylpiperazine (HEP).

As products of the amination reaction, the reaction output may also comprise cyclic ethyleneamines of the general formula

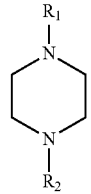

where $R_1$ and $R_2$ are independently or simultaneously either H or a radical of the formula $-(CH_2-CH_2-NH)_x-CH_2-CH_2-NH_2$ where X is an integer in the range from 0 to 4, preferably 0 to 4 and more preferably 1 to 2.

Examples of cyclic ethyleneamines present in the reaction output are piperazine and AEPIP.

The output preferably comprises 1% to 60% by weight of MEA, 1% to 90% by weight of EDA, 0.1% to 30% by weight of higher cyclic ethyleneamines, such as PIP and AEPIP, 0.1% to 30% by weight of higher linear ethyleneamines, such as DETA, TETA and TEPA.

The output more preferably comprises 10% to 50% by weight of MEA, 25% to 85% by weight of EDA, 0.25% to 10% by weight of cyclic ethyleneamines, such as PIP and AEPIP, 1% to 30% by weight of higher linear ethyleneamines, such as DETA, TETA and TEPA.

The output most preferably comprises 15% to 45% by weight of MEA, 30% to 70% by weight of EDA, 0.5% to 5% by weight of cyclic ethyleneamines, such as PIP and AEPIP, 5% to 25% by weight of higher linear ethyleneamines, such as DETA, TETA and TEPA.

The process of the invention can achieve selectivity quotients SQ of 1.5 or more, preferably 2 or more and more preferably of 4 or more. This means that the product ratio of desired linear ethyleneamines and ethanolamines, such as MEA and EDA, to unwanted cyclic ethyleneamines and unwanted higher ethanolamines, such as PIP and AEEA, can be increased by the process of the invention.

The output is generally worked up, such that the different components are separated from one another.

For this purpose, the reaction output is appropriately decompressed.

The components that are in gaseous form after the decompression, such as hydrogen and inert gases, are generally separated from the liquid components in a gas-liquid separator. The gaseous components can be recycled into the amination reactor individually (after a further workup step) or together.

After hydrogen and/or inert gas has been separated off, the output from the amination reactor optionally comprises ammonia, unconverted ethylene glycol and/or monoethanolamine, water and the amination products.

Preferably, the output from the amination reactor is separated in two separation sequences, where each separation sequence comprises a multistage distillation. Such a workup is described, for example, in EP-B1-198699. Accordingly, in the first separation sequence, water and ammonia are first separated off and, in the second separation sequence, a separation into unconverted MEG, and MEA, EDA, PIP, DETA, AEEA and higher ethyleneamines. In this case, lower- and higher-boiling components relative to the azeotrope of MEG and DETA are first removed and then the mixture that has been concentrated in MEG and DETA is separated by extractive distillation with triethylene glycol (TEG) as selective solvent into a stream comprising MEG and DETA. MEA can be recycled partly or fully into the process of the invention with unconverted MEG, optionally together or separately.

ADVANTAGES

In the process of the invention, it is possible to convert MEG and/or MEA with a high selectivity for the linear amination products DETA and EDA, while the selectivity for the cyclic amination product PIP and the higher ethanolamine AEEA is low.

A measure of this effect is the selectivity quotient SQ which is defined as the quotient of the sum total of the selectivities of MEA and EDA and the sum total of the selectivities of PIP and AEEA (SQ=(S(DETA)+S(EDA))/(S(PIP)+S(AEEA)).

The achievement of a high selectivity quotient SQ is industrially advantageous since the market demand for the linear amination products MEA and EDA and their higher homologs, such as DETA and TETA, is higher than the demand for PIP or AEEA.

In addition, the process of the invention forms a lower level of unwanted by-products. Unwanted by-products are, for example, gaseous breakdown products or insoluble or sparingly soluble oligomers and polymers based on MEA and EDA. The formation of such by-products leads to a reduction in the carbon balance and hence to a reduction in the economic viability of the process. The formation of sparingly soluble or insoluble by-products can lead to deposition on the amination catalysts which reduces the activity of the amination catalysts.

The process of the invention likewise leads to a reduction in the amount of N-methylethylenediamine (NMEDA). NMEDA is an unwanted by-product. In many industrial applications, a purity of EDA is specified where the proportion of NMEDA is below 500 ppm by weight.

In addition, it has been found that the catalyst precursors used in the process of the invention have a high activity in the process, and so a favorable space-time yield can be achieved.

Overall, the process of the invention can achieve an advantageous spectrum of properties in relation to overall selectivity, selectivity quotient, activity and the formation of unwanted by-products.

The invention is illustrated by the following examples:

PREPARATION OF THE CATALYST PRECURSORS

Comparative Example 1

85.62 g of cobalt nitrate hexahydrate were dissolved in about 80 ml of hot demineralized water and 269.75 g of Ru nitrosylnitrate solution (16% by weight of Ru) were added thereto. The solution thus obtained was made up to a total of 371 mL with demineralized water.

The metal salt solution thus obtained was transferred to a spray vessel. 500 g of $Al_2O_3$ support (1-2 mm spall) were calcined under an air atmosphere at 900° C.

Thereafter, the maximum water absorption of the support was determined. This was 0.78 mL/g. The spall was impregnated with the metal salt solution prepared beforehand. The amount of the solution corresponds to 95% of the maximum water absorption of the spall.

The spall impregnated with the metal salt solution was then dried at 120° C. in an air circulation drying cabinet for 12 h.

After the drying, the catalyst precursor was reductively calcined under the conditions listed in table 1.

TABLE 1

| | Duration (min) | Temperature (°C.) | Heating rate (°C./min) | Gas flow rate (L (STP)/h) | | | Comment |
|---|---|---|---|---|---|---|---|
| | | | | Nitrogen | Hydrogen | Air | |
| 1 | 30 min | RT | none | 100 | — | — | Purging operation at RT |
| 2 | 150 min | 150 | 1 | 95 | 5 | — | Heating to 150° C. |
| 3 | 120 min | 150 | none | 95 | 5 | — | Hold time at 150° C. |
| 4 | 50 min | | 1 | 95 | 5 | — | Heating to 150° C. |
| 5 | 15 min | 200 | none | 95 | 5 | — | Increase in the amount of hydrogen |
| 6 | 15 min | 200 | none | 90 | 10 | — | Increase in the amount of hydrogen |
| 7 | 15 min | 200 | none | 80 | 20 | | Increase in the amount of hydrogen |
| 8 | 15 min | 200 | none | 70 | 30 | | Increase in the amount of hydrogen |
| 9 | 15 min | 200 | none | 60 | 40 | | Increase in the amount of hydrogen |
| 10 | 15 min | 200 | none | 50 | 50 | | Cooling procedure to RT |
| 11 | 120 min | 200 | none | 50 | 50 | | Hold time at 200° C. |

After the reductive calcination, the catalyst was passivated by subjecting the catalyst to a gas flow of 98 L (STP)/h of N2 and 2 L (STP)/h of air at room temperature. The amount of air was increased gradually, while the amount of N2 was reduced slowly, until 20 L (STP)/h of N2 and 18 L (STP)/h of air were attained. The increase in the amount of air was conducted in such a way that the catalyst temperature did not exceed 35° C.

Comparative Example 2

8.73 g of cobalt nitrate hexahydrate (20.25% by weight of Co) and 1.85 g of nickel nitrate hexahydrate (19% by weight of Ni) formed the initial charge.

56.85 g of Ru nitrosylnitrate solution (16% by weight of Ru) were added to the mixture. The solution thus obtained was made up to a total of 74 mL with demineralized water.

The metal salt solution thus obtained was transferred to a spray vessel. 150 g of Al2O3 support (1-2 mm spall) was calcined at 900° C. under an air atmosphere. Thereafter, the maximum water absorption was determined. This was 0.55 mL/g.

The catalyst support was impregnated with the metal salt solution prepared beforehand in a rotary pan to 90% of the water absorption, by spraying the spall in the rotary pan with the appropriate amount of the metal salt solution.

The spall impregnated with the metal salt solution was subsequently dried at 120° C. in an air circulation drying cabinet for 16 h.

After the drying, the catalyst precursor was reductively calcined under the conditions specified in table 1, comparative example 1.

After the reductive calcination, the catalyst was passivated by subjecting the catalyst to a gas flow of 50 L (STP)/h of N2 and 0 L (STP)/h of air at room temperature. The amount of air was increased gradually, while the amount of N2 was reduced gradually, until the levels reached 20 L (STP)/h of N2 and 20 L (STP)/h of air. The amount of air was increased in such a way that the catalyst temperature did not exceed 35° C.

Comparative Example 3

8.73 g of cobalt nitrate hexahydrate (20.25% by weight of Co) and 1.45 g of copper nitrate hydrate (26.3% by weight of Cu) formed the initial charge. 56.85 g of Ru nitrosylnitrate solution (16% by weight of Ru) were added to the mixture. The solution thus obtained was made up to a total of 74 mL with demineralized water.

The metal salt solution thus obtained was transferred to a spray vessel.

150 g of Al2O3 support (1-2 mm spall) was calcined at 900° C. under an air atmosphere. Thereafter, the maximum water absorption was determined. This was 0.55 mL/g.

The catalyst support was impregnated with the metal salt solution prepared beforehand in a rotary pan to 90% of the water absorption, by spraying the spall in the rotary pan with the metal salt solution.

The spall impregnated with a metal salt solution was subsequently dried at 120° C. in an air circulation drying cabinet for 16 h.

After the drying, the catalyst precursor was reductively calcined and passivated as in comparative example 2.

Comparative Example 4

The preparation was analogous to the preparation of comparative example 1.

The difference, however, was that the reductive calcination was performed at a higher temperature (240° C. rather than 200° C.) according to the conditions that follow (see table 2),

TABELLE 2:

| | Duration (min) | Temperature (°C.) | Heating rate (°C./min) | Gas flow rate (L (STP)/h) | | | Comment |
|---|---|---|---|---|---|---|---|
| | | | | Nitrogen | Hydrogen | Air | |
| 1 | 30 min | RT | none | 100 | — | — | Purging operation at RT |
| 2 | 150 min | 150 | 1 | 95 | 5 | — | Heating to 150° C. |
| 3 | 120 min | 150 | none | 95 | 5 | — | Hold time at 150° C. |

TABELLE 2:-continued

| Duration (min) | Temperature (°C.) | Heating rate (°C./min) | Gas flow rate (L (STP)/h) | | | Comment |
|---|---|---|---|---|---|---|
| | | | Nitrogen | Hydrogen | Air | |
| 4   80 min | 240 | 1 | 95 | 5 | — | Heating to 240° C. |
| 5   15 min | 240 | none | 95 | 5 | — | Increase in the amount of hydrogen |
| 6   15 min | 240 | none | 90 | 10 | — | Increase in the amount of hydrogen |
| 7   15 min | 240 | none | 80 | 20 | | Increase in the amount of hydrogen |
| 8   15 min | 240 | none | 70 | 30 | | Increase in the amount of hydrogen |
| 9   15 min | 240 | none | 60 | 40 | | Increase in the amount of hydrogen |
| 10  15 min | 240 | none | 50 | 50 | | Cooling procedure to RT |
| 11  120 min | 240 | none | 50 | 50 | | Hold time at 240° C. |

Example 1

A catalyst precursor was prepared according to example B3 of WO 2013/072289.

The tablets thus obtained (3*3 mm) were comminuted to 1-2 mm spall. The maximum water absorption capacity of the spall was 0.30 mL/g.

A metal salt solution was prepared. For this purpose, 20.25 g of cobalt nitrate hexahydrate (20.25% by weight of Co) were dissolved in hot water, and 37.91 g of Ru nitrosylnitrate solution were added. The solution thus obtained was made up to 71 mL with demineralized water and transferred to a spray vessel.

The spall was sprayed in an impregnating apparatus with an amount corresponding to 95% of the maximum water absorption of the spall. In order to ensure homogeneous uptake of the impregnation solution, the spall was rotated for a further 30 min. Thereafter, the catalyst spall was dried in an air circulation drying cabinet at 120° C. for 16 h.

The catalyst precursor thus obtained was reductively calcined and passivated as described in comparative example 1.

Example 2

A catalyst precursor was prepared according to example B3 of WO 2013/072289.

The tablets thus obtained (3*3 mm) were comminuted to 1-2 mm spall. The water absorption of the spall was 0.30 mL/g.

A metal salt solution was prepared. For this purpose, 20.25 g of cobalt nitrate hexahydrate (20.25% by weight of Co) were dissolved in hot water, and 37.91 g of Ru nitrosylnitrate solution were added. The solution thus obtained was made up to 71 mL with demineralized water and transferred to a spray vessel.

The spall was sprayed in an impregnation apparatus with an amount that corresponds to 95% of the maximum water absorption of the spall. In order to ensure homogeneous uptake of the impregnation solution, the spall was rotated for a further 30 min.

Thereafter, the catalyst spall was dried in an air circulation drying cabinet at 120° C. for 16 h.

The catalyst precursor thus obtained was reductively calcined and passivated as described in comparative example 4.

A catalyst precursor was prepared according to example B3 of WO 2013/072289. Rather than Al2O3, ZrO2 was used.

The tablets thus obtained (3*3 mm) were comminuted to 1-2 mm spall. The water content of the spall was 0.20 mL/g.

A metal salt solution was prepared. For this purpose, 20.25 g of cobalt nitrate hexahydrate (20.25% by weight of Co) were dissolved in hot water, and 37.91 g of Ru nitrosylnitrate solution were added. The solution thus obtained was made up to 71 mL with demineralized water and transferred to a spray vessel.

The spall was sprayed in an impregnation apparatus with an amount that corresponds to 95% of the maximum water absorption of the spall. In order to ensure homogeneous uptake of the impregnation solution, the spall was rotated for a further 30 min.

Thereafter, the catalyst spall was dried in an air circulation drying cabinet at 120° C. for 16 h.

The catalyst precursor thus obtained was reductively calcined and passivated as described in comparative example 4.

Example 4

A catalyst precursor was prepared according to example B3 of WO 2013/072289. However, 50% of the $Al_2O_3$ support was replaced by ZrO2.

The tablets thus obtained (3*3 mm) were comminuted to 1-2 mm spall. The water content of the spall was 0.24 mL/g.

A metal salt solution was prepared. For this purpose, 20.25 g of cobalt nitrate hexahydrate (20.25% by weight of Co) were dissolved in hot water, and 37.91 g of Ru nitrosylnitrate solution were added. The solution thus obtained was made up to 71 mL with demineralized water and transferred to a spray vessel.

The spall was sprayed in an impregnation apparatus with an amount that corresponds to 95% of the maximum water absorption of the spall. In order to ensure homogeneous uptake of the impregnation solution, the spall was rotated for a further 30 min.

Thereafter, the catalyst spall was dried in an air circulation drying cabinet at 120° C. for 16 h.

The catalyst precursor thus obtained was reductively calcined and passivated as described in comparative example 4.

Example 5

A catalyst precursor was prepared according to example B3 of WO 2013/072289. Rather than 2.4 kg of Al2O3, however, only 0.9 kg of $Al_2O_3$ was used.

The tablets thus obtained (3*3 mm) were comminuted to 1-2 mm spall. The water absorption of the spall was 0.31 mL/g.

A metal salt solution was prepared. For this purpose, 20.25 g of cobalt nitrate hexahydrate (20.25% by weight of Co) were dissolved in hot water, and 37.91 g of Ru nitrosylnitrate solution were added. The solution thus obtained was made up to 71 mL with demineralized water and transferred to a spray vessel.

The spall was sprayed in an impregnation apparatus with an amount that corresponds to 95% of the maximum water absorption of the spall. In order to ensure homogeneous uptake of the impregnation solution, the spall was rotated for a further 30 min.

Thereafter, the catalyst spall was dried in an air circulation drying cabinet at 120° C. for 16 h.

The catalyst precursor thus obtained was reductively calcined and passivated as described in comparative example 4.

Example 6

A catalyst precursor was prepared according to example B3 of WO 2013/072289. The tablets thus obtained (3*3 mm) were comminuted to 1-2 mm spall. The water content of the spall was 0.25 mL/g.

Two metal salt solutions were prepared. To this end, 7.52 g of cobalt nitrate hexahydrate (20.25% by weight of Co) was dissolved in hot water. The solution thus obtained was made up to 28 mL with demineralized water. 19.66 g of Ru nitrosylnitrate solution were made up to 28 mL with demineralized water. The spall was sprayed in an impregnation apparatus with an amount that corresponds to 70% of the maximum water absorption of the spall. The Ru solution was added to the spall first. This was followed by drying in an air circulation drying cabinet at 120° C. for 16 h. Thereafter, the Co solution was added to the spall. Thereafter, the catalyst spall was dried again in an air circulation drying cabinet at 120° C. for 16 h.

The catalyst precursor thus obtained was reductively calcined and passivated as described in comparative example 4.

Catalyst Testing:

The catalysts were tested in a continuously operated parallel plant on the pilot plant scale. The reaction part of the plant consists of eight individual reactors, of which four each are encompassed within one reactor block (heating block). Each individual reactor is a stainless steel tube of length 1.5 m with an internal diameter of 8 mm. The tubes are installed in an electrically heated reactor block consisting of an Al—Mg alloy.

The catalyst was introduced into the reactor in the form of spall (1.5 mm-2 mm) and borne on an inert bed of length about 33 cm consisting of glass beads of size 3 mm.

Above the catalyst bed there is a further, adjoining inert bed of length 15 cm consisting of glass beads of size 3 mm.

The catalyst and the inert bed were fixed in the reactor by a fabric wire of length 1 cm.

Each reactor was operated in straight pass and the flow was from the bottom.

The liquid reactant was supplied from a reservoir with the aid of an HPLC pump. Hydrogen, nitrogen and ammonia were supplied through separate pipelines.

Samples of the liquid reactor outputs were taken from a separator beyond the reactor exit. The reaction outputs were analyzed by gas chromatography.

The catalyst was activated prior to the reaction at 200° C. and 170 bar over a period of 18 h in a 50:50 mixture of hydrogen and nitrogen.

All catalysts were tested under the following conditions:
Temperature: 165° C.
Pressure: 170 bar
H2: 5 L (STP)/h
N2: 10 L (STP)/h
Molar NH3:MEG ratio=10:1
Catalyst hourly space velocity: 0.3 kg/L/h-0.5 kg/L/h
Catalyst volume: 50 mL The exact conditions are summarized in table 3 below.

TABLE 3

| Catalyst | Cat. HSV/ kg/L/h | Conversion/ area % | EDA/ area % | DETA/ area % | AEEA/ area % | PIP/ area % | MEA/ area % | NMEDA + NEEDA + EA/area % | Tot. sel. (5 main products)/ area % | (EDA + DETA)/ (PIP + AEEA) |
|---|---|---|---|---|---|---|---|---|---|---|
| Comparative example 1 | 0.3 | 46.6 | 20.1 | 2.3 | 2.2 | 5.7 | 11.7 | 2.5 | 90.2 | 2.9 |
| Comparative example 2 | 0.3 | 18.5 | 10.3 | 0.4 | 0.2 | 0.4 | 6.7 | 0.3 | 97.1 | 17.9 |
| Comparative example 3 | 0.3 | 12.4 | 7.0 | 0.1 | 0.1 | 0.2 | 4.9 | 0.1 | 98.3 | 30.6 |
| Example 1 | 0.3 | 36.4 | 14.0 | 2.7 | 2.0 | 4.7 | 11.3 | 0.1 | 95.1 | 2.5 |
| Comparative example 4 | 0.3 | 40.0 | 22.1 | 1.7 | 1.2 | 3.7 | 8.9 | 1.3 | 94.2 | 4.9 |
| Example 2 | 0.3 | 41.4 | 15.9 | 3.2 | 2.1 | 7.4 | 10.5 | 0.2 | 94.5 | 2.0 |
| Example 3 | 0.3 | 34.8 | 14.2 | 1.5 | 1.9 | 3.7 | 12.2 | 0.1 | 97.4 | 2.8 |
| Example 4 | 0.3 | 35.7 | 15.1 | 1.5 | 1.6 | 2.7 | 13.7 | 0.1 | 97.1 | 3.8 |
| Example 5 | 0.3 | 28.1 | 11.7 | 1.1 | 1.2 | 2.0 | 11.4 | 0.1 | 97.6 | 4.0 |
| Example 6 | 0.3 | 36.8 | 18.5 | 2.4 | 1.2 | 3.9 | 9.9 | 0.1 | 97.1 | 4.6 |

Comparative example 1 shows that catalyst precursors comprising solely Ru and Co do show high activity but have low selectivity and additionally form a greater amount of unwanted by-products, such as NMEDA.

Comparative examples 2 and 3 show that catalyst precursors that, in addition to Ru and Co, also comprise Ni (comparative example 2) or Cu (comparative example 3)but no Sn—do have a good selectivity but show only low activity.

Only catalyst precursors comprising the inventive combination of Ru, Co and Sn (example 1) show both high activity and high selectivity. Moreover, only a small amount of unwanted by-products, such as NMEDA, is formed.

These observations are confirmed by a comparison of comparative example 4 with examples 2 to 6. By comparison with comparative example 4, the catalyst precursors of examples 2 to 6 comprise not only Co and Ru but additionally Sn. Only catalyst precursors that comprise not only Co and Ru but additionally Sn have the desired combination of properties of a high selectivity, a high activity and a small proportion of unwanted compounds such as NMEDA.

The invention claimed is:

1. A process for preparing alkanolamines and/or ethyleneamines in the liquid phase, by reacting ethylene glycol and/or monoethanolamine with ammonia in the presence of an amination catalyst comprising Co, Ru and Sn and wherein the catalyst is prepared by the reduction of a catalyst precursor and the preparation of the catalytic precursor consists essentially of the steps of
(i) Contacting a catalytic support material with one or more soluble compounds of active metals and optionally one or more soluble compounds of additional catalytic elements with a solution comprising such compounds;
(ii) Optionally, working up the catalyst precursor comprising the steps of separating the catalytic precursor from the solution and optionally washing and drying the separated catalytic precursor;
(iii) Subjecting the separated catalytic precursor to a reductive calcination step;
and wherein steps (i) and (ii) can be repeated one or more times before performing step (iii).

2. The process according to claim 1, wherein the catalyst precursor comprises
0.01% to 20% by weight of catalytically active components of Ru, calculated as RuO; and
1% to 50% by weight of catalytically active components of Co, calculated as CoO; and
0.1% to 5% by weight of catalytically active components of Sn, calculated as SnO.

3. The process according to claim 1, wherein the catalyst precursor comprises one or more added catalyst elements selected from the group consisting of Cu, Ni, Zr and Al.

4. The process according to claim 3, wherein the catalyst precursor comprises
(i) 0.2% to 5% by weight of catalytically active components of Sn, calculated as SnO,
(ii) 1% to 35% by weight of catalytically active components of Co, calculated as CoO,
(iii) 10% to 80% by weight of catalytically active components of Al and/or Zr, calculated as $Al_2O_3$ and $ZrO_2$ respectively;
(iv) 1% to 35% by weight of catalytically active components of Cu and/or 1% to 35% by weight of catalytically active components of Ni, calculated as CuO and NiO respectively; and
(v) 0.01% to 20% by weight of catalytically active components of Ru, calculated as RuO.

5. The process according to claim 1, wherein the catalyst precursor is prepared by coprecipitation.

6. The process according to claim 1, wherein the catalyst precursor is prepared by precipitative application or impregnation.

7. The process according to claim 1, wherein the catalyst precursor is prepared by precipitative application or coprecipitation and is impregnated in a further step.

8. The process according to claim 7, wherein a catalyst precursor comprising only with a portion of the active metals Ru, Co and Sn is prepared by coprecipitation or precipitative application and the missing active metals or the missing portion of the active metals are applied to the catalyst precursor in a subsequent impregnation step.

9. The process according to claim 8, wherein a catalyst precursor comprising the active metals Co and Sn is first prepared and is then contacted in a further impregnation step with the active metals Co and Ru.

10. The process according to claim 9, wherein a catalyst precursor is prepared by precipitative application of the soluble compounds of Co and Sn to a support material and the catalyst precursor thus obtained is contacted with a soluble compound of Ru and a soluble compound of Co in an impregnation step.

11. The process according to claim 10, wherein Sn nitrate and Co nitrate are precipitated onto a support material in the presence of complexing agents and the catalyst precursor thus obtained is contacted with a soluble compound of Ru and a soluble compound of Co in an impregnation step.

12. The process according to claim 1, which further the reductive calcination is in the presence of hydrogen and an inert gas.

13. The process according to claim 12, wherein hydrogen is present in an amount from 1 to at most 50% by volume.

14. A process for preparing alkanolamines and/or ethyleneamines in the liquid phase, by reacting ethylene glycol and/or monoethanolamine with ammonia in the presence of an amination catalyst comprising Co, Ru and Sn and wherein a catalyst precursor is reductively calcined and wherein the catalyst precursor comprises
0.01% to 20% by weight of catalytically active components of Ru, calculated as RuO;
1% to 50% by weight of catalytically active components of Co, calculated as CoO; and
0.1% to 5% by weight of catalytically active components of Sn, calculated as SnO.

15. A process for preparing alkanolamines and/or ethyleneamines in the liquid phase, by reacting ethylene glycol and/or monoethanolamine with ammonia in the presence of an amination catalyst comprising Co, Ru and Sn and
wherein the catalyst is prepared by the reduction of a catalyst precursor and the preparation of the catalytic precursor comprising the steps of
(i) Contacting a catalytic support material with one or more soluble compounds of active metals and optionally one or more soluble compounds of additional catalytic elements with a solution comprising such compounds;
(ii) Optionally working up the catalyst precursor comprising the steps of separating the catalytic precursor from the solution and optionally washing and drying the separated catalytic precursor;
(iii) Subjecting the separated catalytic precursor to a reductive calcination step;
and wherein steps (i) and (ii) can be repeated one or more times before performing step (iii) and with the proviso that an oxidative calcination step conducted in the presence of oxidizing gases is excluded after step (i) or step (ii), respectively.

16. The process according to claim 14, wherein the catalyst precursor comprising only with a portion of the active metals Ru, Co and Sn is prepared by coprecipitation or precipitative application and the missing active metals or the missing portion of the active metals are applied to the catalyst precursor in a subsequent impregnation step.

17. The process according to claim 1, wherein the reductive calcination step is conducted in the presence of inert gas at temperature from 200 to 300° C.

18. The process according to claim 15, wherein the reductive calcination step is conducted in the presence of inert gas at temperature from 200 to 300° C.

19. The process according to claim 14, wherein the catalyst precursor comprises a support material.

20. The process according to claim 19, wherein the support material is aluminum oxide, zirconium oxide or mixtures thereof.

21. The process according to claim 20, wherein the median diameter $d_{50}$ of the support material particles is in the range from 1 to 500 µm.

* * * * *